United States Patent
Shibata et al.

[11] Patent Number: 5,908,747
[45] Date of Patent: *Jun. 1, 1999

[54] MUTANT GENE CAUSING A DEFECT IN MITOCHONDRIAL RECOMBINATION AND A METHOD FOR ITS DETECTION

[75] Inventors: Takehiko Shibata; Feng Ling, both of Saitama; Fusao Makishima, Tokyo, all of Japan

[73] Assignee: Institute of Physical and Chemical Research, Saitama, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/668,448

[22] Filed: Jun. 21, 1996

[30] Foreign Application Priority Data

Jun. 23, 1995 [JP] Japan ..................................... 7-157942
Oct. 3, 1995 [JP] Japan ..................................... 7-256164

[51] Int. Cl.⁶ .............................. C12Q 1/68; C07H 21/04
[52] U.S. Cl. ........................... 435/6; 435/449; 435/320.1; 536/23.5; 536/24.31
[58] Field of Search ................................ 435/4, 6, 320.1, 435/449; 536/23.1, 23.5, 24.31

[56] References Cited

PUBLICATIONS

Feng Ling et al., "A Nuclear Mutation Defective in Mitochondrial Recombination in Yeast," *The EMBO Journal*, vol. 14, No. 16, pp. 4090–4101, 1995.

Kei–ichi Nakagawa, et al., "An Endonuclease With Multiple Current Sites, Endo. ScеI, Initiates Genetic Recombination at its Cutting Site in Yeast Mitochondria", *The EMBO Journal*, vol. 11, No. 7, pp. 2707–2715, 1992.

Helmut Bertrand, et al., "Hyperactive Recombination in the Mitochondrial DNA of the Natural Death Nuclear Mutant of Neurospora Crassa", *Molecular and Cellular Biology*, vol. 13, No. 11, pp. 6778–6788, 1993.

*Primary Examiner*—Carla J. Myers
*Attorney, Agent, or Firm*—Limbach & Limbach LLP

[57] ABSTRACT

A multi-step method of detecting a gene in a nuclear chromosome which is involved in mitochondrial recombination is disclosed. The method disclosed includes the steps: a) fusing enucleated $\omega^-$ mitochondrial donor cells expressing a first marker gene with nucleus-containing $\omega^+$ mitochondrial recipient cells expressing a second marker gene different from the first marker gene to form fused cells wherein the fused cells have one type of mitochondria and b) selecting fused cells that are $\omega^+$ and express the first and second marker genes to identify those enucleated $\omega^-$ mitochondrial donor cells with a reduced recombination frequency. The method includes the further steps of judging that the gene in a nuclear chromosome of the recipient cells involved in mitochondrial recombination is normal when the mitochondrial recombination frequency is high or that the gene is mutated when the recombination frequency is low. The judging steps permit the detection of a mutant gene in a nuclear chromosome of the recipient cells used for cell fusion. An isolated mhr1 and MHR1 gene coding for a polypeptide is also disclosed.

18 Claims, 1 Drawing Sheet

MUTANT GENE CAUSING A DEFECT IN MITOCHONDRIAL RECOMBINATION AND A METHOD FOR ITS DETECTION

FIELD OF THE INVENTION

The present invention relates to a mutant gene (mhr1) in a nuclear chromosome which causes a defect in the homologous recombination of mitochondria as well as a method for detecting the gene.

BACKGROUND OF THE INVENTION

Mitochondria are organelles present in eukaryotic cells and they play a role in synthesizing ATP, which is energy source between generated by oxidative phosphorylation of substances, through an electron transport system.

Mitochondria contain high levels of reactive oxygen species as by-products of oxygen respiration. Reactive oxygen species are continually damaging mitochondrial DNA oxidatively. In order to maintain their DNA and their functions as organelles, mitochondria must have a mechanism for repairing such damage to DNA and suppressing mitochondrial DNA abnormalities. Homologous recombination is believed to be indispensable in the repairing of eukaryotic nuclear DNA as well as bacterial and viral DNA.

Homologous recombination is a phenomenon universally observed in the world of organisms. Homologous recombination may occur, when a DNA molecule has a region having an almost identical base sequence with a base sequence of a region of another DNA molecule allowing the, pairing or the DNA molecules over several hundred base pairs. DNA chains of the two molecules are cut and re-linked to a different chain from the initial one at a site correctly corresponding with each other in those regions. As a result of homologous recombination, damage to one DNA molecule may be complemented by the other DNA. Thus, it is very likely that homologous recombination could play an important and general role in mitochondrial DNA repair.

When the activity of a gene inducing homologous recombination (hereinafter referred to as a "homologous recombination gene") is reduced, it becomes impossible to repair damaged DNA. Thus DNA abnormalities will increase. Furthermore, when a homologous recombination gene functions abnormally, abnormal unequal crossover will occur between a pair of repeated sequences located at sites other than those of alleles. As a result, DNA abnormalities such as deletions are induced. Deletion in mitochondrial DNA has been shown to be associated with mitochondrial diseases (e.g., mitochondrial myopathy which is caused by lack of an enzyme in the energy producing system of mitochondria), aging and the like [Holt, I. J. et al., Nature (London), 331:717–719 (1988)].

Therefore, by isolating a mutant gene involved in those abnormalities in homologous recombination described above and finding out the role of such a gene, it will become possible to use the detection and modification of such a mutant gene in the diagnosis or treatment of mitchondria-related diseases as well as in the prevention of aging and the like.

Most of mitochondrial proteins are encoded by DNAs located on nuclear chromosomes. It is thus expected that the homologous recombination in mitochondrial will be dependent on the genetic information contained in nuclei.

Therefore, as one step to elucidate the role and mechanism of mitochondrial homologous recombination, it is necessary to isolate a gene having a mutation which causes a defect in mitochondrial homologous recombination, i.e., a mutant gene in nuclei.

Conventionally, yeast has been considered as the most appropriate system for obtaining genetic information concerning mitochondria (information on the role of mitochondrial homologous recombination).

Even in yeast, however, it has been extremely difficult to examine a large number of clones for a mutant gene, in particular a recessive mutant gene in a nuclear chromosome involved in mitochondrial homologous recombination. In order to identify such a gene, it is necessary to carry out a mating experiment for detecting the recombination of mitochondria. However, when cells having a recessive mutant gene for mitochondrial homologous recombination are mated with cells having a normal gene for the recombination, the recessive mutant gene is hidden by the function of the normal gene and thus the recessive mutant gene cannot be detected.

Therefore, in the conventional method for isolating a recessive mutant gene in a nuclear chromosome, the following operations are required for the isolation; i) constructing monoploid cells of both alleic mating types (a and α) each having the same nuclear genotype as that of respective mutant monoploid cells; ii) introducing mitochondria having different gene markers into either an a- or α-derivative through the isolation and cell fusion experiments of a ρ-derivative (derivative having no mitochondrial gene) ; and iii) carrying out a mating experiment between a-monoploid and α-monoploid in order to determine the recombination frequency of the mitochondrial gene markers. However, these operations are complicated and time-consuming and it has been extremely difficult to examine a large number of candidate cells simultaneously.

SUMMARY OF THE INVENTION

It is an object of the present invention to provide a gene in nuclear chromosome that induces the homologous recombination in mitochondria, a mutant gene thereof and a method for detecting the mutant gene.

As a result of intensive and extensive research toward the solution of the above goal, the present inventor has identified a method which detects a mutant gene in a cell nucleus involved in mitochontrial homologous recombination by fusing nucleus-containing cells with nucleus-eliminated cells. Further, the inventor has succeeded in cloning the mutant gene and the present invention has been thus achieved.

The present invention relates to a method for detecting a mutant gene in a nuclear chromosome which is involved in mitochondrial homologous recombination, comprising fusing nucleus-containing cells containing mitochondria having a marker gene (I) with nucleus-eliminated cells containing mitochondria having a marker gene (II) different from the marker gene (I), selecting from the resultant fused cells those cells containing recombinant mitochondria having both the marker genes (I) and (II) and determining the presence or absence of the mutant gene based on a decline in the frequency of occurrence of those fused cells containing recombinant mitochondria.

As a mutant gene, a recessive mutant gene such as mhr1 gene may be considered. As a marker gene (I) or (II), the chloramphenicol resistance gene, the oligomycin resistant gene or the antimycin resistance gene may be enumerated. Here, it should be noted that the marker gene (I) and the marker gene (II) are two different genes.

The present invention further relates to an mhr1 gene coding for a polypeptide comprising the amino acid sequence for the wild-type MHR1 protein shown in SEQ ID NO. 1, the sequence having a mutation in at least one amino acid residue at position 99. As the sequence having a mutation, the sequence depicted in SEQ ID NO. 2 may be given.

"MHR1 protein" used herein means a protein obtainable by expressing MHR1 gene (a wild-type gene in a cell nucleus inducing the homologous recombination of mitochondria). "An mhr1 gene" used herein means a mutant of MHR1 gene, i.e., a mutant gene in a cell nucleus which induces a defect in mitochondrial homologous recombination.

An "amino acid sequence having a mutation" used herein means an amino acid sequence which is encoded by a gene having a function to cause a defect in mitochondrial homologous recombination and which is the amino acid sequence shown in SEQ ID NO. 1 having a substitution, addition or deletion of at least one amino acid residue including the one at position 99.

Therefore, it means that as long as the amino acid sequence has a substitution, addition or deletion of the amino acid residue at position 99 mentioned as described above and yet has a function to cause a defect in mitochondrial homologous recombination, the amino acid sequence may have other substitutions, additions or deletions of amino acid residues at positions other than 99.

The present invention further relates to a recombinant plasmid comprising the gene described above.

DETAILED DESCRIPTION OF THE INVENTION

Hereinbelow, the present invention will be described in detail.

For the cloning of the gene of the invention, first the presence or absence of a mutant gene causing a defect in mitochondrial homologous recombination is determined. Subsequently, into those cells which were found to have a mutant gene of interest as a result of the above detection, a yeast genomic library containing wild-type genes is introduced, and then the target wild-type gene is cloned. This cloning is achieved by probing a gene which complements the mutation concerning specific properties varied in mutant cells (e.g., defect in DNA damage repairment, defect in recombination, or temperature sensitivity mutation, etc.). In other words, the cloning is achieved by probing the wild-type gene corresponding to the mutant gene. Subsequently, in order to clone the mutant gene of the invention, primers are designed based on the nucleotide sequence for the wild-type gene. Then, PCR is carried out using the total genomic DNA of the mutant cell as a template. Finally, the nucleotide sequence of the mutant gene obtained is determined and a site of mutation is ascertained by comparing the resultant sequence with the nuoleotide sequence for the wild-type gene. Thus, the gene of the invention can be cloned.

1. Detection of a Mutant Gene

The detection of a mutant gene of interest is carried out by fusing nucleus-containing cells containing mitochondria having a specific marker gene (e.g., an antibiotic resistance gene) with nucleus-eliminated cells containing mitochondria having a different marker gene from the above marker gene, measuring the frequency of mitochondrial homologous recombination by selecting from the resultant fused cells those cells containing recombinant mitochondria based on individual resistance against a specific antibiotic corresponding to the marker gene, and determinig from a decline in the frequency the presence or absence of a mutation in a gene involved in mitocondrial homologous recombination. Here, the presence or absence of a mutant gene can be determined regardless of whether the mutant gene is dominant or recessive.

The procedures for the detection are as follows and FIG. 1 shows an outline thereof.

In FIG. 1, first two kinds of cells used in cell fusion are prepared.

One is prepared as a recipient cell 1 and the other as a donor cell 2.

The recipient cell 1 is the cell which will be the target for detection and has a nucleus 5 and mitochondria 3 . In the nucleus 5 , there exists any one of the following three genes: a normal mitochondrial homologous recombination gene, a recessive mutant gene thereof or a dominant mutant gene thereof. As examples of recipient cells 1 , yeast cells or cultured animal or plant cells may be enumerated.

On the other hand, the donor cell 2 is the cell which will supply mitochondria 4 contained in it to the recipient cell 1 . The doner cell 2 has been deprived of a nucleus 6 in advance by treatment with a drug (e.g., nocodazole). Thus, it is a nucleus-eliminated cell containing the mitochondria 4 but not the nucleus 6 . Consequently, whether the mitochondria in the recipient cell 2 will undergo homologous recombination or not has nothing to do with the genetic information contained in the nucleus 6 . As the donor cell 2 , a cell of the same organism species as that of the recipient cell 1 may be used.

The preparation of cells, passage of cells, subculture and the like may be carried out using conventional techniques.

The DNA in the mitochondria 3 in the recipient cell 1 and the DNA in the mitochondria 4 in the donor cell 2 respectively contain a discrete marker gene. One resistance gene in the mitochondria 3 is designated as a marker gene (I) and the other resistance gene in the mitochondria 4 as a marker gene (II). These marker genes will become necessary in the process of selecting specific fused cells as described later. For example, when a marker gene (I) is the chloramphenicol resistance gene, this gene will be required if the selection is carried out using chloramphenicol; and when a marker gene (II) is the oligomycin resistance gene, this gene will be required if the selection is carried out using oligomycin.

The marker genes (I) and (II) are two different genes and there is no particular limitation to their kinds. For example, the chloramphenicol resistance gene, the oligomycin resistance gene or the antimycin resistance gene may be used in an appropriate combination.

In the present invention, for the purpose of explanation, the chloramphenicol resistance gene (hereinafter referred to as "Chl$^R$") is used as a marker gene (I) in the mitochondria 3 in the recipient cell 1 and the oligomycin resistance gene (hereinafter referred to as "Oli$_1$$^R$" is used as a marker gene (II) in the mitochondria 4 in the donor cell 2 as one illustration.

Subsequently, the recipient cell 1 is fused with the donor cell 2 by a cell fusion method. The cell fusion may be carried out by a conventional cell fusion method using polyethylene glycol after the removal of cell walls of both cells with an appropriate drug (e.g., lyticase). Conventional methods may also be used for the regeneration of cell walls.

When the cell fusion has been carried out normally, the mitochondria 3 and the mitochondria 4 are contained in mixture in the new recipient cell (i.e., fused cell 7). After the cell fusion, the homologous recombination of mitochondrial DNA is dependent on (is governed by) only the genetic information contained in the nucleus 5 from the recipient cell 1. At this stage, however, it is still unknown whether the homologous recombination gene in the nucleus 5 is a normal gene, a recessive mutant or a dominant mutant.

Then, only those cells having the nucleus 5 are selected by culturing cells on a medium to which canavanine [2-amino-4-(guanidinoxy)butyric acid] has been added. For this purpose, the chromosomes of the nucleus 5 have been so engineered to contain a canavanine-resistance recessive mutant gene such as "can1". As a result, cells having the nucleus 6 which are inevitably mixed in the donor cells or diploid cells which are generated as a result of fusion with the cells having the nucleus 6 are completely removed. During the course of this culture, individual cells begin to contain either the mitochondria 3, mitochondria 4 or recombinant mitochondria 8 alone.

Subsequently, from the resultant fused cells, those fused cells containing mitochondria containing a gene from other mitochondria, eg. $Oli_1^R$ (the marker gene from recipient cells 1) are selected by culturing the cells on an oligomycin-added medium. Then, those cells containing recombinant mitochondria containing a gene from other mitochondria, eg. $Chl^R$ (the marker gene from donor cells 2) are selected by culturing the cells on a chloramphenicol-added medium.

When the homologous recombination gene in the nucleus 5 is a mutant gene, this gene cannot work properly in mitochondrial homologous recombination and, as a result of the cell fusion and the subsequent culture, the mitochondria 3 or the mitochondria 4 exist alone in fused cells 7. Accordingly, cells containing the mitochondria 3 and cells containing the mitochondria 4 are removed by oligomycin and chloramphenicol, respectively, and finally, no cells containing recombinant mitochondria are obtained.

On the other hand, when the homologous recombination gene in the nucleus 5 is a normal gene, this gene works properly in the homologous recombination of the DNA of the mitochondria 3 with the DNA of the mitochondria 4 and, as a result, the mitochondria 8 are obtained in which two kinds of mitochondria derived from the recipient cell 1 and the donor cell 2 are recombined (i.e., recombinant mitochondria having both marker genes $Chl^R$ and $Oli_1^R$ in one mitochondrial DNA). Accordingly, only those cells containing the mitochondria 8 can survive through the selection with oligomycin and chloramphenicol and are obtained as a resultant product.

When cells containing recombinant mitochondria have been obtained finally, the nucleus 5 in the recipient cell 1 can be judged to have a normal gene for mitochondrial homologous recombination. On the other hand, when cells containing recombinant mitochondria have not been obtained, the nucleus 5 in the recipient cell 1 can be judged to have a recessive or dominant mutant gene for the recombination.

The judgment as to whether the mutant gene is a dominant gene or a recessive gene may be made by comparing the occurrence frequency of the recombinants obtained by the method of the invention with the occurrence frequency of the recombinants obtained by the conventional method (a method wherein nucleus-containing donor cells are fused with recipient cells). Briefly, the mutant gene-containing monoploid cells are mated with a normal gene-containing monoploid cells by the conventional method. As a result, if diploid cells containing recombinant mitochondria have occurred at the same frequency as that observed in the case of mating a normal gene-containing monoploid cells with each other, the mutant gene is judged a recessive mutant gene. On the other hand, the mutant gene is judged a dominant gene when no diploid cells containing recombinant mitodhondria have occurred.

2. The Cloning of the Gene

The causative gene, which is either dominant or recessive, detected by the above procedures is cloned by techniques of molecular biology.

In the present invention, MHR1 which is a wild-type yeast DNA is cloned first in order to obtain a recessive mutant gene (mhr1) in a nuclear chromosome that impairs the homologous recombination of mitochondrial DNA. Then, PCR is carried out using as primers the base sequences of flanking regions contiguous to the open reading frame of the obtained wild-type MHR1 gene and using as a template the total DNA of those cells containing the mutant gene of interest. The mutant gene can be cloned by these procedures.

(1) Preparation of a Wild-Type Yeast Genomic DNA Library

The extraction of chromosomal DNA from the wild-type cells as detected by the procedures described above may be carried out by any of the conventional methods.

Subsequently, the chromosomal DNA obtained is completely digested with the restriction enzyme Sau3AI to thereby obtain Sau3AI fragments of the chromosomal DNA. The Sau3AI fragments are then subjected to conventional agarose gel electrophoresis and a piece of gel containing a fragment of the desired chain length is cut out.

The DNA fragment in the cut out gel is purified with phenol/chloroform or the like and then concentrated by ethanol precipitation or the like, to thereby obtain a purified fragment.

The purified Sau3AI fragment is inserted into an appropriate vector at its BamHI restriction site to thereby prepare a recombinant DNA. A genomic DNA library can be prepared by transforming or transducing a host cell using this recombinant DNA.

As a host cell, E. coli DH5 α or JM109 may be used.

(2) Extraction of Plasmid DNA

The genomic library obtained is introduced into a mutant. The method for transforming yeast is as described below [H. Ito et al., J. Bacteriol. 153 (1983), 163].

Mutant cells which have grown on YPD liquid medium (1% yeast extract, 2% polypeptone and 2% glucose) at 30° C. are treated with 1 mM lithium chloride in the presence of 10 mM Tris-HCl buffer (pH 7.5). Subsequently, the genomic library is treated with lithium chloride in the presence of approx. 75 mg of salmon sperm dissolved in 1 ml of TE [10 mM Tris-HCl, 1 mM EDTA (pH 8.0)] and 40% polyethylene glycol 4000 and then introduced into the mutant cells.

The thus transformed mutant cells are seeded on histidine and tryptophan-containing SD agar medium (a medium containing 2% glucose, 0.67% amino acid-free yeast extract and 2% agar) and growing colonies are obtained. The obtained colonies are replicated on a glycerol-containing agar medium and those colonies growing at 37° C. are obtained.

The obtained colonies are cultured on histidine and tryptophan-containing SD liquid medium (2% glucose, 0.67% amino acid-free yeast extract) to thereby obtain cultured cells. The obtained yeast cells are disrupted with glass beads and the resultant cell-free extract is introduced into E. coli (e.g., DH5 α), which is then spread on ampicillin-containing LB agar medium (1% bacto-tryptone, 0.5% yeast extract, 0.5% NaCl, 2% agar, pH 7.2). By further culturing grown colonies on ampicillin-containing LB liquid medium, plasmid DNA can be extracted.

(3) The Subcloning of the DNA and Determination of the Base Sequence thereof

The plasmid DNA obtained above is digested with restriction enzymes such as ClaI, BamHI and MluI to thereby cut out DNA fragments. From these fragments, those DNA fragments are subcloned which exhibit complementation for the defect in recombination, temperature sensitivity mutation, defect in the repairing of DNA damage induced by UV irraditation, and the like of the mhr1 mutant. This subcloning is carried out by inserting each of short DNA fragments into plasmid YCp50 and introducing these DNA fragments into mutant cells according to the method for transforming yeast as described above [H. Ito et al., J. Bacteriol. 153 (1983), 163]. The shortest DNA fragment obtained is further inserted into plasmid pUC118. Then, the base sequence of the fragment is determined by a known method (for example, dideoxyribonucleotide sequencing, Maxam-Gilbert method and the like).

In addition, the location of this gene in yeast chromosomes can be ascertained by conducting Southern hybridization on 16 yeast chromosomes separated by pulsed field gel electrophoresis using a fragment of this gene as a probe.

(4) The Cloning of mhr1 Gene and Determination of the Site of Mutation

The mhr1 gene in the mutant is cloned and, further, the site of mutation in the gene is ascertained.

First, the total genomic DNA is prepared from the mhr1 mutant. Briefly, mhr1 mutant cells which have grown on YPD liquid medium at 30° C. for 48 hours are treated with Zymolyase-100T (Seikagaku Corporation, Tokyo, Japan) to thereby remove cell walls. Then, the resultant cells are disrupted in the presence of 1% SDS (sodium lauryl sulfate). From the resultant extract, the total genomic DNA of the mhr1 mutant is prepared according to conventional procedures for DNA separation and purification (C. Guthrie and G.R. Fink, Molecular Biology, Academic Press Inc., San Diego, Calif., 1991).

PCR is conducted on the total genomic DNA obtained from the mhr1 mutant. For this PCR, the base sequences for the peripheral regions of the open reading frame of the above-described cloned MHR1 gene are used as primers (primers can be obtained by chemical synthesis). This PCR may be conducted using a reaction solution containing 10 mM Tris-HCl, 1.5 mM $MgCl_2$, 50 mM KCl, 0.125 mM each dNTP, 1 pmol primers and 1.25 units of taq DNA polymerase (Boehringer Mannheim).

Subsequently, the mhr1 gene obtained is inserted into pUC118 at the Hinc II site and the base sequence thereof is determined. The sequencing method is the same as described above.

Figure 1:
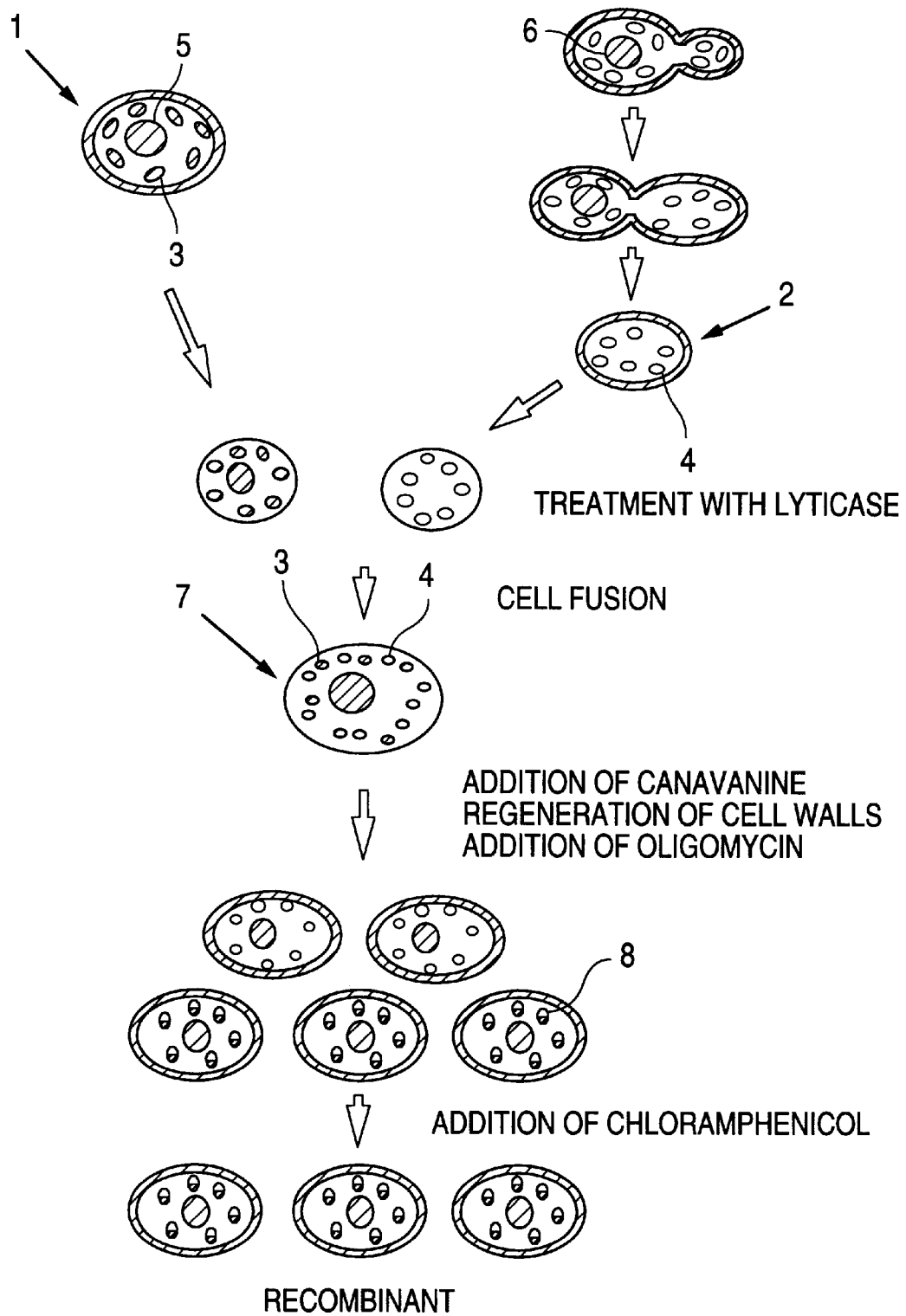
FIG. 1 shows an outline of the method for detecting a mutant gene involved in mitochondrial homologous recombination.

1. Recipient cell; 2. Donor cell; 3. Mitochondrion; 4. Mitochondrion; 5. Nucleus; 6. Nucleus; 7. Fused cell; 8. Mitochondrion containing a recombinant DNA

EXAMPLES

Hereinbelow, the present invention will be described in more detail with reference to the following Examples. However, the present invention is not limited to these Examples.

Example 1

Detection of a Mutant Gene (1) Preparaton of Donor Cells

In order to prepare donor cells exhibiting the mitochondrial genotype of $\omega^-$-$Oli_1^R$ ("$\omega^-$" means there is no $\omega$·intron in the mitochondrial genes and "$\omega^+$" means there are $\omega$·introns in the mitochondrial genes), OP11c-55R5 cells (derived from the yeast *Saccharomyces cerevisiae*) were suspended in a 50 ml Falcon tube at a density of $1.5 \times 10^6$ cells/ml in 10 ml of YPGly medium to which 15 µ/ml of nocodazole (which inhibits the transfer of nuclei when daughter cells are newly formed; see Jacobs, C. W. et al., J. Cell Biol., 107, 1409–1426 (1988); manufactured by Sigma) containing 1% DMSO had been added.

After incubation at 18° C. for 20 hours, four tubes (individually containing approx. $2.2 \times 10^6$ cells/ml) were centrifuged (1,400×g, at 4° C. for 5 min) and then washed once with 20 ml of KPS buffer (1.2M sorbitol, 50 mM potassium phosphate buffer, pH 7.5) per one tube. Then, the cells were recovered in one 50 ml tube (Falcon). In order to separate nucleus-eliminated cells from mother cells, the recovered cells were resuspended in 10 ml of KPS buffer and sonicated with a sonifier cell disrupter (Model UR-200P, Tommy Seiko) at 0° C. for 3 minutes (intensity 4/11).

The present inventor confirmed that completely nucleus-eliminated cells had been formed in the suspension by examining the cells after DAPI-dyeing with a fluorescent microscope and a phase contrast microscope. The treated suspension was centrifuged (1,400×g, at 4° C. for 5 min) and the resultant precipitate was resuspended in 200 µl of KPS buffer. This suspension was subjected to density gradient centrifugation in a glass tube (12.5 mm in dia.×105 mm in length) using 1 ml of 10%, 15%, 20%, 25% and 30% Ficoll 400 (Pharmacia Bioprocess Technology AB). After the suspension was gradient-centrifuged at 150×g for 30 minutes at 30° C., 15% Ficoll fraction contained nucleus-eliminated cells by about 70% in the microscopic observation after DAPI dyeing. Accordingly, the 15% Ficoll fraction was recovered and diluted twofold with KPS buffer. Then, the resultant solution was centrifuged at 1,400×g for 5 minutes at 30° C. to thereby recover cells. After the cells were washed with 3 ml of KPS buffer once, the mixture of mother cells and nucleus-eliminated cells was centrifuged at 1,400×g for 5 minutes at 30° C. and then resuspended in 1 ml of KPS buffer.

OP11c-55R5 cells described above are designated as *Saccharomyces cerevisiae* OP11-55R5 and have been deposited at the National Institute of Bioscience and Human-technology, Agency of Industrial Science and Technology under the accession No. FERM BP-5551.

(2) Preparaton of Recipient Cells

IL166-187 cells, a mutant thereof and UV11 cells were prepared as recipient cells. IL166-187 cells, which are a strain of the yeast *Saccharomyces cerevisiae*, contain "MHR1" (a normal gene) in their nuclei and are wild-type cells exhibiting the mitochondrial genotype "$\omega^+$ $Chl^R$". FL67 cells, which are a mutant of IL166-187 cell strain, were obtained by introducing a mutation into IL166-187 cells by an ethylmethane sulfonate treatment. FL67 cells have the mutant gene "mhr1" in their nuclei and exhibit the mitochondrial genotype "$\omega^+$ $Chl^R$". UV11 cells were also prepared by treating IL166-187 cells in a similar manner to that employed in the preparation of FL67 cells. UV11 cells had in their nucleus a mitochondrial homologous recombination gene which was not known as to whether normal, recessive mutant or dominant mutant. UV11 cells exhibits the mitochondrial genotype "$\omega^+$ $Chl^R$".

IL166-187 cells are designated as *Saccharomyces cerevisiae* IL166-187 and FL67 cells as *Saccharomyces cerevisiae* FL67. The former and the latter have been deposited at the National Institute of Bioscience and Human-technology, Agency of Industrial Science and Technology under the accession Nos. FERM BP-5552 and FERM BP-5550, respectively.

(3) Cell Fusion

The suspension of nucleus-eliminated cells and mother cells (i.e., the donor cell prepared in (1) above) and each of the three recipient cells prepared in (2) above were mixed in a ratio of 3:1 ($3 \times 10^6$ cells: $1 \times 10^6$ cells) in 100 μl of KPS buffer. To the resultant mixture, 50 units of lyticase (Boehinger Mannheim GmbH, 10,000 unit/ml) was added and kept at 30° C. for 30 minutes to thereby form spheroplasts (cells from which cell walls have been removed). The spheroplasts were recovered by centrifuging the mixture at 1,000×g for 5 minutes at 30° C. The recovered spheroplasts were washed with 1 ml of KPS buffer twice, centrifuged at 1,000×g for 5 minutes at 30° C. and then recovered. In order to carry out cell fusion using the spheroplasts, the pellet was suspended in 250 μl of 35% polyethylene glycol 4000 (dissolved in KPS buffer), kept at 30° C. for 15 minutes and centrifuged at 1,000×g for 5 minutes at 30° C., to thereby precipitate spheroplasts. The spheroplasts were washed with 1 ml of KPS buffer once and then suspended in 2 ml of SD medium to which necessary amino acids and canavanine (1.5 μg/ml) had been added (in a glass tube 12.5 mm in dia.×105 mm in length). The suspension was incubated at 30° C. under rotary shaking (at 93 rpm for 3 days). Subsequently, the culture was diluted 100-fold and incubated for another 3 days under the same conditions as described above. As a result, fused cells were obtained which contain a nucleus derived from the recipient cell.

(4) Treatment with Antibiotics (Selection of Cells)

Subsequently, the fused cells described above were seeded on YPGly plate containing oligomycin (3 μg/ml) to thereby select those cells which had received the $Oli_1^R$-mitochondria marker from the donor cell. Colonies exhibiting resistance against oligomycin ($Oli_1^R$) were cultured on YPG plate containing chloramphenicol (4 mg/ml) and oligomycin. The percent (%) of chloramphenicol resistant ($Chl^R$) colonies in $Oli_1^R$ colonies was calculated as a gene conversion frequency at position ω. Gene conversion is a type of genetic recombination.

(5) Results

The results are shown in Table 1. In Table 1, a capital letter indication (e.g., MHR1) in a parenthesis provided under a recipient cell name means that the gene of interest in the nucleus of this cell is a normal gene. A small letter indication (e.g., mhr1) in a parenthesis provided under a recipient cell name means that the gene of interest in the nucleus of this cell is a mutant gene. What are indicated in blankets are genotypes of mitochondria. The meanings of $\omega^+$, $\omega^-$ $Chl^R$ and $Oli_1^R$ are the same as described previously. (These explanations will also apply to Table 2).

TABLE 1

| No. | Recipient Cell | Donor Cell | $Oli_1^R$ Colony | $Chl^R$ Colony | % $Chl^R/Oli^R$ Recombinant |
|---|---|---|---|---|---|
| 1 | IL166-187 (MHR1) [$\omega^+$ $Chl^R$] | OP11c-55R5 [$\omega^-$ $Oli_1^R$] | 284 | 279 | 98.2 |
| 2 | FL67 (mhr1) [$\omega^+$ $Chl^R$] | OP11c-55R5 [$\omega^-$ $Oli_1^R$] | 23 | 1 | 4.3 |
| 3 | UV11 (Unknown) [$\omega^+$ $Chl^R$] | OP11c-55R5 [$\omega^-$ $Oli_1^R$] | 28 | 27 | 96.5 |

From Table 1, it has been found that the recipient IL166-187 cells do not have a mutant gene of interest because the genes in their nuclei have induced mitochondrial monologous recombination (98.2% of recombinants were obtained). On the other hand, it has been found that FL67 cells have a mutant gene of interest because the genes in their nuclei have not induced mitochondrial monologous recombination (only 4% of recombinants were obtained). Further, it has been found that UV11 cells do not have a mutant gene involved in homologous recombination.

Comparative Example 1

An assay was carried out to determine whether the mutant gene contained in FL67 cells is recessive or dominant by the conventional method in which a donor cell is used without the elimination of its nucleus (i.e., a method in which two monoploid cells having different mating types (α and a) are mated with each other). Recipient and donor cells used for this assay were IL166-187 and its derivative, derivatives of FL67, and derivatives of UV11. All of these cells were prepared by the inventor by treatment with ethylmethane sulfonate.

The results are shown in Table 2.

TABLE 2

| No. | α Cell | α Cell | $Oli_1^R$ Colony | $Chl^R$ Colony | % $Oli_1^R/Chl^R$ Recombinant |
|---|---|---|---|---|---|
| 4 | 1L166-187 (MHR1) [$\omega^+$ $Chl^R$] | IL1666b-55R5 (MHR1) [$\omega^-$ $Oli_1^R$] | 703 | 690 | 98.2 |
| 5 | FL67-55R5 (mhr1) [$\omega^-$ $Oli_1^R$] | FL67-2c (mhr1) [$\omega^+$ $Chl^R$] | 825 | 312 | 37.8 |
| 6 | FL67-55R5 (mhr1) [$\omega^-$ $Oli_1^R$] | IL166-6b (MHR1) [$\omega^+$ $Chl^R$] | 287 | 273 | 95.1 |
| 7 | UV11-55R5 (UV11) [$\omega^-$ $Oli_1^R$] | UV11-1a (UV11) [$\omega^+$ $Chl^R$] | 423 | 418 | 98.8 |

As seen from Table 2, when one of the two monoploid cells mated as a normal gene of interest (see No. 6, for example) in its nucleus, this normal gene induces mitochondrial homologous recombination regardless of whether a gene of interest in the nucleus of the other cell has a mutation or not. This result is in constast with the result of No. 2 in Table 1.

Therefore, the mutant gene (mhr1) in the nucleus of FL67 cells is found to be a recessive mutant gene which is hidden by a corresponding normal gene in the donor cell and eventually allows mitochondrial homologous recombination to occur.

As so far described, even a recessive mutant gene can be detected the detection method of the invention.

Example 2

The Cloning of MHR1 Gene

In order to obtain those genes governing the phenotypes of the mutant FL67 (mhr1) (a defect in the repairing of DNA damage caused by UV irradiation, a defect in recombination and a temperature sensitivity mutation), the cloning of MHR1 gene was carried out focusing on a gene which complements the temperature sensitivity mutation.

(1) Construction of a Genomic Library

A genomic library for MHR1 gene was constructed using the wildtype yeast cell IL166-187 (FERM BP-5552) described in Example 1 by conventional methods. For the construction, YCp50 which is a single copy vector was used.

Subsequently, the yeast genomic library constructed with YCp5 was introduced into the mhr1 mutant FL67 (FERM BP-5550; MET α, ura3, his1, trp1) as described below.

Mutant cells grown on YPD liquid medium (1% yeast extract, 2% polypeptone and 2% glucose) at 30° C. was treated with 1 mM lithium chloride in the presence of 10 mM Tris-HCl buffer (pH 7.5). Subsequently, the genomic library was treated with lithium chloride in the presence of aprox. 75 mg of salmon sperm dissolved in 1 ml of TE [10 mM Tris-HCl, 1 mM EDTA (pH 8.0)] and 45% polyethylene glycol 4000 and then introduced into the mutant cells.

The thus transformed mutant was seeded on histidine and tryptophan-containing SD agar medium (a medium containing 2% glucose, 0.67% amino acid-free yeast extract and 2% agar) and growing colonies were obtained. The obtained colonies were replicated on a glycerol-containing agar medium and those colonies growing at 37° C. were obtained.

The obtained colonies were cultured on histidine and tryptophan-containing SD liquid medium (2% glucose, 0.67% amino acid-free yeast extract) to thereby obtain cultured cells. The obtained yeast cells were disrupted with glass beads and the resultant cell-free extract was introduced into *E. coli* DH5 α, which was then spread on ampicillin-containing LB agar medium (1% bacto-tryptone, 0.5% yeast extract, 0.5% NaCl, 2% agar, pH 7.2). By further culturing grown colonies on ampicillin-containing LB liquid medium, plasmid DNA was extracted.

More specifically, the transformed mutant cells described above were cultured on SD agar medium (2% glucose, 0.67% amino acid-free yeast extract, 2% agar) containing histidine (8 mg/20 ml plate) and tryptophan (8 mg/20 ml plate) at 30° C. for 5 days and growing colonies were replicated on a glycerol-containing agar medium. Of these colonies, one colony which can grow at 37° C. on the glycerol-containing agar medium was selected to thereby obtain one candidate.

This candidate (colony) was cultured on SD liquid medium (2% glucose, 0.67% amino acid-free yeast extract) containing 2 ml of histidine (8 mg/20 ml plate) and tryptophan (8 mg/20 ml plate) at 30° C. overnight and then the yeast cells were disrupted with glass beads 0.5 mm in size.

The cell-free extract obtained was introduced into *E. coli* DH5 α according to the method of D. Hanahan [J. Mol. Biol., 166 (1983), 557-580]. The resultant *E. coli* cells were spread on LB agar medium (1% bacto triptone, 0.5% yeast extract, 0.5% NaCl, 2% agar, pH 7.2) containing ampicillin (50 μg/ml).

After the cells were cultured for one day at 37° C., one colony was selected from grown colonies and further cultured on LB liquid medium containing ampicillin (50 μg/ml) (at 37° C. for one day).

From these cells, plasmid DNA was extracted by the alkali method (Nucleic Acid Res., 7, 1513). A DNA fragment of 9.6 kbp was contained at the BamHI site of the plasmid obtained.

This DNA fragment of 9.6 kbp was digested with restriction enzymes such as ClaI, BamHI and MluI. The resultant DNA fragments were further subcloned until a DNA fragment of about 0.7 kbp was obtained which exhibited complementation for the recombination and temperature sensitivity of the mhr1 mutant. This fragment was inserted into pUC118 at the HincII site and the base sequence thereof was determined with an A.L.F. DNA Sequencer (Pharmacia).

The results are shown in SEQ ID NO. 3. The base sequence represented by SEQ ID NO. 3 was obtained by cloning a gene which complemented the characteristics of the mutation and this sequence is a base sequence for the wild-type gene of interest. In SEQ ID NO. 3, there was an open reading frame of 459 pb presumably coding for 153 amino acids. The amino acid sequence in this open reading frame is shown in SEQ ID NO. 1.

Southern hybridization of this gene was carried out on 16 yeast chromosomes separated by pulsed field gel electrophoresis using a fragment of this gene as a probe. As a result, it has been made clear that this gene is located on chromosome XII.

Considering that all of the phenotypes the mutant had were complemented by the wild-type gene MHR1, the inventor judged that this gene is truly the gene of interest.

Example 3

The Cloning of mhr1 Gene and Determination of the Site of Mutation

The mhr1 gene of a mutant was cloned and the site of mutation of the gene was ascertained.

The total genomic DNA was obtained from an mhr1 mutant (FL67; FERM BP-5550) by the procedures described below.

Cell walls of mhr1 mutant cells which had grown on YPD liquid medium at 30° C. for 48 hours were removed with Zymolyase-100T (Seikagaku Corporation, Tokyo, Japan). Subsequently, cells were disrupted in the presence of 1% SDS (sodium lauryl sulfate). From the extract obtained, DNA was separated and purified by conventional DNA separation/purification procedures (C. Guthrie and G.R. Fink, Molecular Biology, Academic Press Inc., San Diego, Calif., 1991) to thereby prepare the total genomic DNA of the mhr1 mutant.

PCR was conducted on 100 ng of of the total genomic DNA obtained in a reaction solution containing 10 mM Tris-HCl, 1.5 mM $MgCl_2$, 50 mM KCl, 0.125 mM each dNTP, 1 pmol primers and 1.25 units of tag DNA polymerase (Boehringer Mannheim). Incubation at 94° C. for 25 seconds, subsequent annealing at 55° C. for 30 seconds and polymerase reaction at 68° C. for 1 minute composed one cycle and 35 cycles were conducted. Thereafter, the period of the polymerase reaction conducted at 68° C. was extended to 7 minutes. As primers, a forward primer (SEQ ID NO. 5) and a reverse primer (SEQ ID NO. 6) were used.

The mhr1 gene obtained was inserted into pUC118 at the Hinc II site and the base sequence thereof was determined.

The results are shown in SEQ ID NO. 4.

In SEQ ID NO. 4, one mutation (substitution of G with A) was found at position 296 in the open reading frame shown in SEQ ID NO. 3 (i.e. at position 421 in the base sequence of SEQ ID NO. 3). Due to this mutation, it is presumed that the amino acid at position 99 has been changed from glycine to aspartic acid at the protein level. The thus changed amino acid sequence is shown in SEQ ID NO. 2.

According to the present invention, a mutant gene inducing a defect in mitochondrial homologous recombination and a recombinant plasmid comprising such a gene are provided.

Since the wild-type gene corresponding to the gene of the invention is essential for stabilization and maintenance of mitochondrial DNA which is indispensable for the maintenance of cell respiratory functions in eukaryotes, the gene of the invention is useful for detecting the lowering of respiratory functions associated with the aging of humans and for breeding a strong yeast strain applicable to fermentation production.

What is claimed is:

1. An isolated wildtype MHR1 gene coding for a polypeptide comprising the amino acid sequence shown in SEQ ID NO: 1.

2. A recombinant plasmid comprising the gene of claim 1.

3. An isolated mhr1 gene coding for a polypeptide comprising the amino acid sequence shown in SEQ ID NO: 2.

4. An isolated wildtype MHR1 gene comprising the nucleotide sequence shown in SEQ ID NO: 3.

5. An isolated mhr1 gene comprising the nucleotide sequence shown in SEQ ID NO: 4.

6. A method for detecting a mutant gene on nuclear chromosomes that is required for mitochondrial recombination, comprising:
   (a) fusing recipient cells from a mutant candidate clonal colony or a wild type strain corresponding to the mutant wherein said recipient cells contain mitochondria expressing a first marker gene with enucleated cells containing mitochondria expressing a second marker gene different from the first marker gene;
   (b) selecting the resulting fused cells which express the second marker gene;
   (c) selecting from the fused cells selected in (b) those cells containing recombinant mitochondria expressing both the first and second marker genes;
   (d) calculating recombination frequency by dividing the number of clonal colonies expressing said first marker and said second marker genes in step (c) by the number of colonies expressing said second marker gene in step (b); and
   (e) comparing the recombination frequency of the candidate clonal colony with that of the wild type strain corresponding to the candidate clonal colony wherein a recombination frequency in the mutagenized candidate colony lower than that of the corresponding wild-tyre stain indicates a decrease in the recombination frequency; and
   (f) judging that the gene on nuclear chromosomes of said recipient cells required for mitochondrial recombination is mutated when the recombination frequency of said candidate clonal colony is lower than that of the corresponding wild type strain in the results of step (e), to thereby detect a mutant gene in nuclear chromosomes of the recipient cells used for the cell fusion.

7. A method of detecting a mutant gene in a nuclear chromosome which is involved in mitochondrial recombination, comprising:
   (a) fusing nucleus-containing ω+ mitochondrial recipient cells expressing a first marker gene with enucleated ω− mitochondrial donor cells expressing a second marker gene different from said first marker gene to form fused cells;
   (b-1) selecting a first set of cells from said fused cells in (a), having mitochondria that express at least the second marker gene, and determining the number of said first set of cells ($N_1$),
   (b-2) selecting a second set of cells from said fused cells in (a) having mitochondria that express the first and second marker genes and are ω+ and determining the number of said second set of cells ($N_2$);
   (b-3) dividing $N_2$ by $N_1$ to determine a mitochondrial recombination frequency; and
   (c) judging that the gene in a nuclear chromosome of the recipient cells involved in mitochondrial recombination is normal when the mitochondrial recombination frequency is high, or judging that said nuclear chromosome gene is mutated when said frequency is low, to thereby detect a mutant gene in a nuclear chromosome of the recipient cells used for the cell fusion.

8. A method of detecting a recessive mutant gene in a nuclear chromosome which is involved in mitochondrial recombination, comprising:
   (a) fusing nucleus-containing ω+ mitochondrial recipient cells expressing a first marker gene with enucleated ω− mitochondrial donor cells expressing a second marker gene different from said first marker gene to form fused cells;
   (b-1) selecting a first set of cells from said fused cells in (a), having mitochondria that express at least the second marker gene, and determining the number of said first set of cells ($N_1$),
   (b-2) selecting a second set of cells from said fused cells in (a) having mitochondria that express the first and second marker genes and are ω+ and determining the number of said second set of cells ($N_2$);
   (b-3) dividing $N_2$ by $N_1$ to determine a mitochondrial recombination frequency;

(c) judging that a nuclear chromosome gene of the recipient cells involved in mitochondrial recombination is normal when the mitochondrial recombination frequency is high, or judging that said nuclear chromosome gene is mutated when said frequency is low, to thereby detect a mutant gene in a nuclear chromosome of the recipient cells used for the cell fusion; and (d) determining whether the mutant gene detected is a dominant or recessive mutant gene by a mating assay.

9. The method of claim 8 including the additional step of forming enucleated ω– mitochondrial donor cells by incubating ω– mitochondrial donor cells in nocodazol.

10. The method of claim 8 wherein said first marker gene is a chloramphenicol resistance gene and said second marker gene is an oligomycin resistance gene.

11. The method of claim 6 including the additional step of forming enucleated ω– mitochondrial donor cells by incubating ω– mitochondrial donor cells in nocodazol.

12. The method of claim 6 wherein said first marker gene is a chloramphenicol resistance gene and said second marker gene is an oligomycin resistance gene.

13. A recombinant plasmid comprising the gene of claim 4.

14. A recombinant plasmid comprising the gene of claim 5.

15. A recombinant plasmid comprising the gene of claim 3.

16. The method of claim 7 including the additional step of forming enucleated ω⁻ mitochondrial donor cells by incubating ω⁻ mitochondrial donor cells in nocadazole.

17. The method of claim 7 wherein said first marker gene is a chloramphenicol resistance gene and said second marker gene is an oligomycin resistance gene.

18. The method of claim 8 wherein the recessive mutant gene is an mhr1 gene.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 153 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:1:

```
Met Cys Val Val Asn Leu Gln Asn Tyr Lys Gln Ser Val His Leu Tyr
1               5                   10                  15

Gln Asn Leu Cys Arg Leu Arg Tyr Leu Arg Asp Val Ala Gln Arg Lys
            20                  25                  30

Glu Ser Asp Lys Leu Arg Lys Lys Asp Ser Asn Gly His Val Trp Tyr
        35                  40                  45

Ser Gly Gln Tyr Arg Pro Thr Tyr Cys Gln Glu Ala Val Ala Asp Leu
    50                  55                  60

Arg Glu Ser Leu Leu Lys Val Phe Glu Asn Ala Thr Pro Ala Glu Lys
65                  70                  75                  80

Gln Thr Val Pro Ala Lys Lys Pro Ser Ile Tyr Trp Glu Asp Pro Trp
                85                  90                  95

Arg Met Gly Asp Lys Asp Lys His Trp Asn Tyr Asp Val Phe Asn Ala
            100                 105                 110

Leu Gly Leu Glu His Lys Leu Ile Gln Arg Val Gly Asn Ile Ala Arg
        115                 120                 125

Glu Glu Ser Val Ile Leu Lys Glu Leu Ala Lys Leu Glu Ser His Pro
    130                 135                 140

Thr Glu Gln Thr Glu Val Ser Ser Gln
145                 150
```

(2) INFORMATION FOR SEQ ID NO:2:

(i) SEQUENCE CHARACTERISTICS:
       (A) LENGTH: 153 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:2:

```
Met Cys Val Val Asn Leu Gln Asn Tyr Lys Gln Ser Val His Leu Tyr
1               5                   10                  15

Gln Asn Leu Cys Arg Leu Arg Tyr Leu Arg Asp Val Ala Gln Arg Lys
            20                  25                  30

Glu Ser Asp Lys Leu Arg Lys Lys Asp Ser Asn Gly His Val Trp Tyr
        35                  40                  45

Ser Gly Gln Tyr Arg Pro Thr Tyr Cys Gln Glu Ala Val Ala Asp Leu
    50                  55                  60

Arg Glu Ser Leu Leu Lys Val Phe Glu Asn Ala Thr Pro Ala Glu Lys
65                  70                  75                  80

Gln Thr Val Pro Ala Lys Lys Pro Ser Ile Tyr Trp Glu Asp Pro Trp
                85                  90                  95
```

```
            Arg Met Asp Asp Lys Asp Lys His Trp Asn Tyr Asp Val Phe Asn Ala
                    100                 105                 110

Leu Gly Leu Glu His Lys Leu Ile Gln Arg Val Gly Asn Ile Ala Arg
                    115                 120                 125

Glu Glu Ser Val Ile Leu Lys Glu Leu Ala Lys Leu Glu Ser His Pro
                    130                 135                 140

Thr Glu Gln Thr Glu Val Ser Ser Gln
            145                 150

(2) INFORMATION FOR SEQ ID NO:3:

(i) SEQUENCE CHARACTERISTICS:
           (A) LENGTH: 680 base pairs
           (B) TYPE: nucleic acid
           (C) STRANDEDNESS: double
           (D) TOPOLOGY: linear (ii) MOLECULE TYPE: DNA (genomic)

(vi) ORIGINAL SOURCE:
           (A) ORGANISM: Saccharomyces cerevisiae
           (B) STRAIN: IL166-187

(ix) FEATURE:
           (A) NAME/KEY: CDS
           (B) LOCATION: 126..584

(xi) SEQUENCE DESCRIPTION: SEQ ID NO:3:

AGAGTATGGA CAAGTACTAT ATTCTCAATT TCCCAACTTT TCGCAAACAC AGGTGGATAA        60

GCTGTTTGTG AGACCAAACT GGAGCAACAG AAAGCCATCA TTGAGAAGGG ACATCTGGAA       120

AATGT ATG TGT GTA GTG AAC TTG CAA AAC TAT AAG CAG AGT GTC CAT           167
      Met Cys Val Val Asn Leu Gln Asn Tyr Lys Gln Ser Val His
       1               5                  10

CTA TAC CAG AAC CTC TGC CGG TTG AGA TAC CTC CGT GAT GTG GCA CAG         215
Leu Tyr Gln Asn Leu Cys Arg Leu Arg Tyr Leu Arg Asp Val Ala Gln
 15                  20                  25                  30

CGT AAG GAG AGT GAC AAG CTA AGA AAA AAG GAC TCT AAC GGG CAC GTC         263
Arg Lys Glu Ser Asp Lys Leu Arg Lys Lys Asp Ser Asn Gly His Val
                 35                  40                  45

TGG TAT AGC GGA CAG TAT AGA CCT ACA TAT TGT CAA GAG GCA GTG GCA         311
Trp Tyr Ser Gly Gln Tyr Arg Pro Thr Tyr Cys Gln Glu Ala Val Ala
             50                  55                  60

GAC TTG CGG GAG TCC TTG TTG AAG GTG TTT GAG AAT GCC ACA CCA GCA         359
Asp Leu Arg Glu Ser Leu Leu Lys Val Phe Glu Asn Ala Thr Pro Ala
 65                  70                  75

GAA AAG CAG ACA GTA CCC GCC AAA AAA CCG TCC ATA TAC TGG GAG GAC         407
Glu Lys Gln Thr Val Pro Ala Lys Lys Pro Ser Ile Tyr Trp Glu Asp
 80                  85                  90

CCA TGG AGG ATG GGT GAC AAG GAC AAA CAT TGG AAT TAC GAT GTG TTC         455
Pro Trp Arg Met Gly Asp Lys Asp Lys His Trp Asn Tyr Asp Val Phe
 95                 100                 105                 110

AAT GCT CTG GGG CTG GAA CAC AAG CTT ATT CAG CGT GTG GGG AAC ATT         503
Asn Ala Leu Gly Leu Glu His Lys Leu Ile Gln Arg Val Gly Asn Ile
                115                 120                 125

GCG AGG GAA GAA AGC GTT ATT CTG AAG GAA CTA GCT AAG CTC GAA TCA         551
Ala Arg Glu Glu Ser Val Ile Leu Lys Glu Leu Ala Lys Leu Glu Ser
            130                 135                 140

CAT CCT ACA GAG CAG ACG GAA GTG TCT TCC CAG TAG AACGCTTCGT             597
His Pro Thr Glu Gln Thr Glu Val Ser Ser Gln
            145                 150

CATTAGATAT ACAAATGCAG GTAGAAAAAA AAACATATAT AAGCTCATGT AAATAGTGCA      657
```

ATGCAAACCT TTCTGCCAAA TCC                                                680

(2) INFORMATION FOR SEQ ID NO:4:

(i) SEQUENCE CHARACTERISTICS:
        (A) LENGTH: 680 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Saccharomyces cerevisiae
        (B) STRAIN: FL67

(ix) FEATURE:
        (A) NAME/KEY: CDS
        (B) LOCATION: 126..584

(xi) SEQUENCE DESCRIPTION: SEQ ID NO:4:

AGAGTATGGA CAAGTACTAT ATTCTCAATT TCCCAACTTT TCGCAAACAC AGGTGGATAA      60

GCTGTTTGTG AGACCAAACT GGAGCAACAG AAAGCCATCA TTGAGAAGGG ACATCTGGAA     120

AATGT ATG TGT GTA GTG AAC TTG CAA AAC TAT AAG CAG AGT GTC CAT         167
      Met Cys Val Val Asn Leu Gln Asn Tyr Lys Gln Ser Val His
          155                 160                 165

CTA TAC CAG AAC CTC TGC CGG TTG AGA TAC CTC CGT GAT GTG GCA CAG       215
Leu Tyr Gln Asn Leu Cys Arg Leu Arg Tyr Leu Arg Asp Val Ala Gln
    170                 175                 180

CGT AAG GAG AGT GAC AAG CTA AGA AAA AAG GAC TCT AAC GGG CAC GTC       263
Arg Lys Glu Ser Asp Lys Leu Arg Lys Lys Asp Ser Asn Gly His Val
185                 190                 195

TGG TAT AGC GGA CAG TAT AGA CCT ACA TAT TGT CAA GAG GCA GTG GCA       311
Trp Tyr Ser Gly Gln Tyr Arg Pro Thr Tyr Cys Gln Glu Ala Val Ala
200                 205                 210                 215

GAC TTG CGG GAG TCC TTG TTG AAG GTG TTT GAG AAT GCC ACA CCA GCA       359
Asp Leu Arg Glu Ser Leu Leu Lys Val Phe Glu Asn Ala Thr Pro Ala
            220                 225                 230

GAA AAG CAG ACA GTA CCC GCC AAA AAA CCG TCC ATA TAC TGG GAG GAC       407
Glu Lys Gln Thr Val Pro Ala Lys Lys Pro Ser Ile Tyr Trp Glu Asp
            235                 240                 245

CCA TGG AGG ATG GAT GAC AAG GAC AAA CAT TGG AAT TAC GAT GTG TTC       455
Pro Trp Arg Met Asp Asp Lys Asp Lys His Trp Asn Tyr Asp Val Phe
        250                 255                 260

AAT GCT CTG GGG CTG GAA CAC AAG CTT ATT CAG CGT GTG GGG AAC ATT       503
Asn Ala Leu Gly Leu Glu His Lys Leu Ile Gln Arg Val Gly Asn Ile
    265                 270                 275

GCG AGG GAA GAA AGC GTT ATT CTG AAG GAA CTA GCT AAG CTC GAA TCA       551
Ala Arg Glu Glu Ser Val Ile Leu Lys Glu Leu Ala Lys Leu Glu Ser
280                 285                 290                 295

CAT CCT ACA GAG CAG ACG GAA GTG TCT TCC CAG TAG AACGCTTCGT           597
His Pro Thr Glu Gln Thr Glu Val Ser Ser Gln
                300                 305

CATTAGATAT ACAAATGCAG GTAGAAAAAA AAACATATAT AAGCTCATGT AAATAGTGCA    657

ATGCAAACCT TTCTGCCAAA TCC                                            680

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "(synthetic DNA)"

(xi) SEQUENCE DESCRIPTION: SEQ ID NO:5:

GGACATCTGG AAAATGTATG                                        20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "(synthetic DNA)"

(xi) SEQUENCE DESCRIPTION: SEQ ID NO:6:

TCTAATGACG AAGCGTTCTA                                        20